United States Patent [19]

Taniguchi et al.

[11] Patent Number: 5,089,651
[45] Date of Patent: Feb. 18, 1992

[54] PROCESS FOR PRODUCING 3-IMINONITRILES

[75] Inventors: Masato Taniguchi; Tadahisa Sato; Yuki Mizukawa, all of Kanagawa, Japan

[73] Assignee: Fuji Photo Film Co., Ltd., Kanagawa, Japan

[21] Appl. No.: 636,825

[22] Filed: Jan. 2, 1991

Related U.S. Application Data

[63] Continuation-in-part of Ser. No. 436,271, Nov. 14, 1989, abandoned.

[30] Foreign Application Priority Data

Nov. 14, 1988 [JP] Japan .................. 63-287039

[51] Int. Cl.$^5$ ............................. C07C 253/30
[52] U.S. Cl. ........................ 558/360; 558/378
[58] Field of Search ............. 558/357, 360, 378

[56] References Cited

U.S. PATENT DOCUMENTS 3,290,355  12/1966  Kunisch et al. ............... 558/360

FOREIGN PATENT DOCUMENTS 375067  11/1983  Australia .

OTHER PUBLICATIONS

Reynolds et al., J. of Org. Chem., 16 (No. 2) (1951), pp. 165-172.
Adkins et al., J.A.C.S., 64 (No. 1) (1942), pp. 150-154.

Primary Examiner—Joseph Paul Brust
Attorney, Agent, or Firm—Sughrue, Mion, Zinn, Macpeak & Seas

[57] ABSTRACT

A process for producing a 3-iminonitrile represented by the following general formula (I):

$$CH_3\overset{\overset{NM}{\|}}{C}CH_2CN \qquad (I)$$

wherein M represents an alkali metal, which comprises reacting acetonitrile with an alkali metal hydride in an amount of from 0.01 to 0.5 molar equivalent to acetonitrile; and a process for producing a 3-iminonitrile of the formula (II):

$$CH_3\overset{\overset{NH}{\|}}{C}CH_2CN \qquad (II)$$

which comprises mixing the compound represented by the foregoing general formula (II), which was obtained by the reaction between acetonitrile and the alkali metal hydride, with a protic solvent, are disclosed. These processes are useful for producing the desired 3-iminonitrile safely, inexpensively and in high yields.

10 Claims, No Drawings

PROCESS FOR PRODUCING 3-IMINONITRILES

CROSS-REFERENCE TO RELATED APPLICATIONS

This application is a continuation-in-part application of application Ser. No. 07/436,271, filed Nov. 14, 1989 (abandoned).

FIELD OF THE INVENTION

This invention relates to a process for producing 3-iminonitriles and, more particularly, to a process for producing 3-iminonitriles useful as intermediates for synthesizing photographic couplers or medicines.

BACKGROUND OF THE INVENTION

3-Iminonitriles are useful as intermediates for synthesizing photographic couplers or medicines. For example, 3-iminobutyronitrile is used in JP-A-59-171956 (the term "JP-A" as used herein means an "unexamined published Japanese patent application") corresponding to U.S. Pat. No. 4,540,654 as a starting material for synthesizing 1H-pyrazolo[1,5-b]-1,2,4-triazoles useful as photographic magenta couplers.

As to synthesis of the 3-iminonitriles, descriptions are given in *Journal of the American Chemical Society*, 64, 150 (1942), French Patent No. 1,377,891, *Canadian Journal of Chemistry*, 43, 332 (1965), and Austrian Patent No. 375,067, disclosing, for example, the following synthesizing processes:

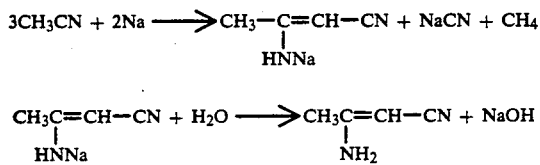

However, these processes result in the undesired production of poisonous sodium prussiate. In addition, in actual production, a step of removing the sodium prussiate is inevitably involved, and therefore the processes involve an additional problem in that production cost of the 3-iminonitriles becomes seriously high.

Further, *The Journal of Organic Chemistry*, Vol. 16, February, 1951, PP. 165–172 describes the following synthetic reaction:

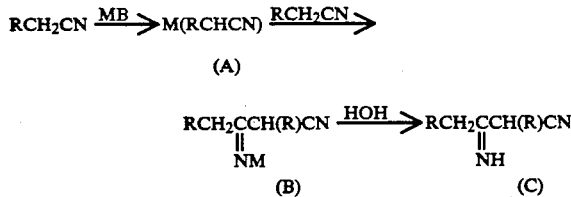

and, in specific embodiments thereof, compounds of formula (C) wherein R is methyl and phenyl are reported as being obtained in a yield of 20% and 78%, respectively, calculated based on the yield of β-ketonitrile obtained by acid hydrolysis of the compound of formula (C). However, with the use of acetonitrile as a starting material of the above reaction, diisopropylaminomagnesium bromide (DIPAM) or sodium is used as a basic reagent. The use of sodium as a basic reagent provides the desired product in high yields, but results in generation of poisonous sodium prussiate as described above, and the use of DIPAM as a basic reagent provides the desired product in a yield of only about 5%.

The above J. Org. Chem reference describes that the use of propionitrile (CH$_3$CH$_2$CN) and DIPAM as a basic reagent at a molar ratio of 1:1 produces the desired compound (C) in 65% yield, whereas the use of acetonitrile and DIPAM at a molar ratio of 1:1 produces the desired compound (C) in only 5% yield. Also, this reference describes that, when propionitrile and NaH as a basic reagent are used at a molar ratio of 1:1, the desired compound (C) can be obtained in a yield of 20%, with a considerable amount of unidentified solid also being produced. Thus, the above J. Org. Chem. reference teaches that (1) the yield of the desired compound produced from acetonitrile is very low as compared with that produced from propionitrile when DIPAM is used as a basic reagent; and (2) the yield of the desired compound produced from propionitrile using NaH as a basic reagent is low as compared with that is obtained by using DIPAM. Contrary to the teachings of the J. Org. Chem. reference, the present invention makes it possible to produce the desired 3-iminonitrile, a dimer of acetonitrile, from acetonitrile using a small amount (from 0.01 to 0.5 molar equivalent) of a metal hydride such as NaH, without producing a trimer of acetonitrile.

SUMMARY OF THE INVENTION

The present invention has been achieved in light of the above-described situation, and an object thereof is to provide 3-iminonitriles with producing substantially no sodium prussiate and, therefore, to synthesize 3-iminonitriles stably, inexpensively and in high yields.

As a result of intensive investigations to solve the problems with the conventional processes, the present inventors have found that 3-iminonitriles can be produced with ease from acetonitrile by using a metal hydride as a base in an amount of from 0.01 to 0.5 molar equivalent to acetonitrile, in place of metallic sodium which is used in the conventional processes.

That is, the present invention provides a process for producing a 3-iminonitrile represented by the following general formula (I):

wherein M represents an alkali metal, which comprises reacting acetonitrile with an alkali metal hydride in an amount of from about 0.01 to about 0.5 molar equivalent to acetonitrile.

In addition, the present invention provides a process for producing a 3-iminonitrile represented by the formula (II):

which comprises mixing the compound represented by the above general formula (I), which was obtained by reaction between acetonitrile and the alkali metal hydride, with a protic solvent.

DETAILED DESCRIPTION OF THE INVENTION

In the present invention, 3-iminonitrile represented by the formula (II) is considered to be isomerized to a 3-aminocrotononitrile, and, therefore, the formula (II) is of course used to represent such a 3-aminocrotononitrile as well.

An embodiment of the present invention is now described in detail below.

Synthesis steps of the present invention are shown by the following process (1):

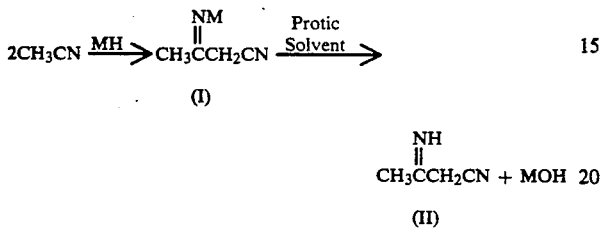

wherein M is as defined above.

In the above reaction, the alkali metal hydride is used in an amount of from about 0.01 to about 0.5 molar equivalent to acetonitrile. The reaction between acetonitrile and the alkali metal hydride can be carried out in the presence of a solvent including acetonitrile. When acetonitrile is used for serving as both the reactant and the solvent, the alkali metal hydride is preferably used in an amount of from 0.01 to 0.2 molar equivalent to the total molar amounts of acetonitrile.

Preferable metal hydrides include lithium hydride, sodium hydride and potassium hydride, with sodium hydride being particularly preferred.

As a reaction solvent to produce the compound of the general formula (I), any of commonly known aprotic solvents with high or low polarity may properly be selected and used alone or as a mixture thereof.

The amount of the solvent is not particularly limited, but it is preserably used in an amount of from about 2 to about 10 times (by weight) as much as acetonitrile as a starting material.

The reaction solvent is preferably acetonitrile, an aromatic hydrocarbon solvent (e.g., benzene, toluene or xylene) or an aliphatic hydrocarbon solvent (e.g., hexane or octane).

A reaction temperature ranging from about 60° C. to about 150° C. is preferred, and, when acetonitrile is used as a solvent, a reaction temperature in a range of from 60° C. to 70° C. is preferred.

Reaction time is preferably about 30 minutes to about 10 hours, with 1 hour to 5 hours being more preferable. However, since the reaction time varies depending upon the scale of the reaction, etc., it is not limited to the above-described range.

The reaction can be conducted under atmospheric pressure.

The compound represented by the general formula (II) can be obtained by mixing the compound obtained by the above-described reaction and represented by the general formula (I) with a protic solvent such as water. The compound of formula (I) need not be isolated from the aprotic solvent used in the above reaction before mixing with a protic solvent. The protic solvent must be used at a molar ratio of at least 2 times as much as the amount of alkali metal hydride used, preferably at a molar ratio of 3 to 5 times as much as the amount of acetonitrile used as the starting material. The mixing procedure is conducted at a temperature of preferably from about 0° C. to room temperature under atmospheric pressure.

The 3-iminonitrile obtained according to process (1) described above can be separated from the reaction solution in a conventional manner but, if necessary, they may be used as the starting material for the subsequent reaction without separation.

As a suitable isolating means, recrystallization, solvent extraction, filtration, column chromatography, thin layer chromatography, etc. may be used independently or in a proper combination.

The present invention is now illustrated in greater detail by reference to the following examples which, however, are not to be construed as limiting the present invention in any way. Unless otherwise indicated, all percents, ratios, parts, etc. are by weight.

EXAMPLE 1

Synthesis of Compound (1)

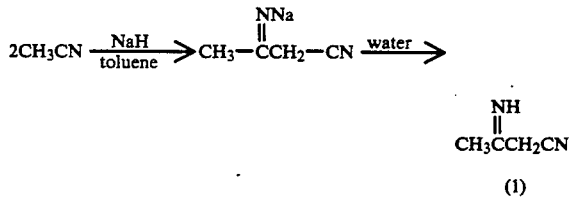

9.6 (2.39×10$^{-1}$ mol) of sodium hydride (60% dispersion in mineral oil) was added to 75 ml of toluene and, under heat-refluxing (at a reaction temperature of 108° C.) and stirring, 25 ml (4.79×10$^{-1}$ mol) of acetonitrile was dropwise added thereto. Refluxing under heat was continued for an additional 3 hours. Thereafter, a precipitate was collected by filtration, and the precipitate was dispersed in diethyl ether, followed by adding water thereto. Then, the organic phase was separated and dried over Glauber's salt, and diethyl ether was distilled off under reduced pressure to obtain 14.5 g of crystals containing Compound (1).

EXAMPLE 2

The synthesis of Compound (1) as well as the preparation of 5-amino-4-chloro-3-methyl-1H-pyrazole hydrochloride (B) which is useful as an intermediate for a photographic coupler from the resulting compound (1) are shown below.

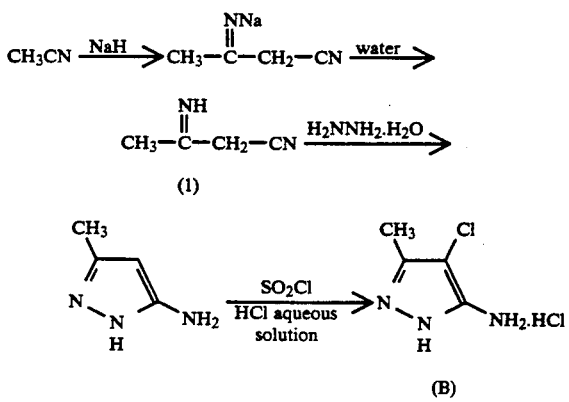

115 g (3.00 mol) of sodium hydride (62.5% dispersion in mineral oil) was added to 922 ml of acetonitrile, and the resulting mixture was stirred while heating at 60° to 70° C. for 2 hours. Thereafter, 300 ml of water and 200 ml of hexane were added to the mixture at a temperature of 30° to 40° C. The reaction mixture separated into three layers, and the intermediate layer was isolated and acetonitrile was distilled off therefrom under reduced pressure. 225 g (3.60 mol) of 80% hydrazine hydrate was added to the residue, and the mixture was heated with stirring at 80° C. for 1 hour and then at 110° to 115° C. for 2 hours. After allowing to cool, 175 ml of acetone was added to the mixture. After heating the mixture at 60° C. for 1 hour while stirring, 40 ml of toluene was added thereto, and the solvent was distilled off under reduced pressure.

420 ml of 36% aqueous hydrochloric acid and 80 ml of water were added to the residue, and 361 ml of sulfuryl chloride was added dropwise thereto over 1 hour while maintaining the reaction system at a temperature of 30° C. or below, during which time crystals precipitated from the reaction system. Then, the reaction mixture was stirred for 4 hours while maintaining at 20° C. or below. Thereafter, the generator $SO_2$ was removed by an aspirator for 2 hours under reduced pressure. The pressure of the reaction system was allowed to raise to atmospheric pressure, and 300 ml of acetone was added thereto, followed by stirring at 6° C. for 2 hours. The filter cake obtained by filtering the reaction mixture was washed with 300 ml of acetone and dried to obtain 37 g of 5-amino-4-chloro-3-methyl-1H-pyrazole hydrochloride (B).

A pyrazoloazole coupler can be prepared from the compound (B), for example, according to the procedure as described in Example 3 at columns 30 to 31 of U.S. Pat. No. 4,540,654.

Pyrazoloazole series couplers can also be synthesized from the 3-iminonitriles produced according to the present invention by, for example, a process shown as process (2) below, starting with the compound represented by the general formula (II).

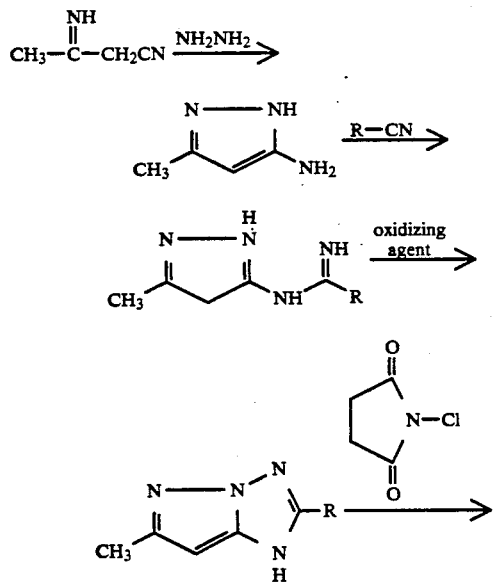

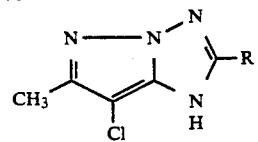

wherein R represents a substituent such as alkyl or aryl.

The process of the present invention enables one to synthesize 3-iminonitrile with more safety, more inexpensiveness and in a higher yield than the conventional processes. Therefore, use of the 3-iminonitrile as an intermediate for synthesizing photographic couplers or medicines and agricultural chemicals is feasible.

While the present invention has been described in detail and with reference to specific embodiments thereof, it is apparent to one skilled in the art that various changes and modifications can be made therein without departing from the spirit and the scope of the present invention.

What is claimed is:

1. A process for producing a 3-iminonitrile represented by the following general formula (I):

wherein M represents an alkali metal, which comprises reacting acetonitrile with an alkali metal hydride in an amount of from 0.01 to 0.5 molar equivalent to acetonitrile.

2. A process for producing a 3-iminonitrile of the formula (II):

which comprises mixing the compound represented by the general formula (I):

wherein M represents an alkali metal, with a protic solvent, wherein said compound represented by the general formula (I) is obtained by reacting acetonitrile with an alkali metal hydride in an amount of from 0.01 to 0.5 molar equivalent to acetonitrile.

3. A process as claimed in claim 1, wherein said alkali metal hydride is lithium hydride, sodium hydride or potassium hydride.

4. A process as claimed in claim 2, wherein said protic solvent is used at a molar ratio of at least 2 times as much as the amount of said alkali metal hydride used.

5. A process as claimed in claim 1, wherein the reaction is conducted in the presence of a solvent.

6. A process as claimed in claim 5, wherein said solvent is an aromatic hydrocarbon solvent or an aliphatic hydrocarbon solvent.

7. A process as claimed in claim 5, wherein said solvent is benzene, toluene, xylene, hexane .or octane.

8. A process as claimed in claim 5, wherein said solvent is acetonitrile.

9. A process as claimed in claim 1, wherein the reaction is conducted at a temperature in the range of from about 60° C. to about 150° C.

10. A process as claimed in claim 8, wherein the reaction is conducted at a temperature in the range of from about 60° C. to about 70° C.

* * * * *